(12) United States Patent
Morinaka et al.

(10) Patent No.: US 8,604,150 B2
(45) Date of Patent: *Dec. 10, 2013

(54) EPOXY GROUP-CONTAINING ORGANOSILOXANE COMPOUND, CURABLE COMPOSITION FOR TRANSFER MATERIALS AND METHOD FOR FORMING MICROPATTERN USING THE COMPOSITION

(75) Inventors: Katsutoshi Morinaka, Minato-ku (JP); Yoshikazu Arai, Minato-ku (JP); Hiroshi Uchida, Minato-ku (JP); Toshio Fujita, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 224 days.

This patent is subject to a terminal disclaimer.

(21) Appl. No.: 12/741,148

(22) PCT Filed: Nov. 5, 2008

(86) PCT No.: PCT/JP2008/070122
§ 371 (c)(1),
(2), (4) Date: May 3, 2010

(87) PCT Pub. No.: WO2009/060862
PCT Pub. Date: May 14, 2009

(65) Prior Publication Data
US 2010/0258983 A1  Oct. 14, 2010

(30) Foreign Application Priority Data
Nov. 7, 2007  (JP) .................................. 2007-289470

(51) Int. Cl.
*C08G 77/08*  (2006.01)
(52) U.S. Cl.
USPC ................... 528/15; 528/31; 528/26; 528/27; 522/148
(58) Field of Classification Search
USPC ............................ 528/15, 26, 27, 31; 522/148
See application file for complete search history.

(56) References Cited

U.S. PATENT DOCUMENTS

| 5,204,433 A * | 4/1993 | Wewers et al. .................... 528/12 |
| 6,716,992 B2 * | 4/2004 | Musa ............................. 548/453 |
| 7,034,089 B2 * | 4/2006 | Herr et al. ...................... 525/479 |
| 7,880,018 B2 * | 2/2011 | Sasaki et al. ................... 548/406 |
| 2009/0182110 A1 * | 7/2009 | Sasaki et al. ..................... 528/26 |
| 2009/0263631 A1 | 10/2009 | Sakamoto et al. |

FOREIGN PATENT DOCUMENTS

| CN | 1880322 | * | 12/2006 |
| JP | 58-222160 A | | 12/1983 |
| JP | 2003-048988 A | | 2/2003 |
| JP | 2003-100609 A | | 4/2003 |
| JP | 2004-262952 A | | 9/2004 |
| JP | 2005-042050 A | | 2/2005 |
| JP | 2005-277280 A | | 10/2005 |
| JP | 2006-177989 A | | 7/2006 |
| JP | 2007-72374 A | | 3/2007 |
| WO | 2007-142248 | * | 12/2007 |
| WO | 2008-020637 | * | 2/2008 |
| WO | 2008/020637 A1 | | 2/2008 |

OTHER PUBLICATIONS

Tao et al., "Synthesis and characterization fo imide ring and siloxane-containing cycloaliphatic epoxy resins", European Polymer Journal, Apr. 2007, pp. 1470-1479.*
English language translation CN 1880322, Dec. 2006.*
Xing Cheng, et al., "Room-Temperature, Low-Pressure Nanoimprinting Based on Cationic Photopolymerization of Novel Epoxysilicone Monomers", Advanced Materials, 2005, pp. 1419-1424, vol. 17, No. 11.

* cited by examiner

*Primary Examiner* — Margaret Moore
(74) *Attorney, Agent, or Firm* — Sughrue Mion, PLLC

(57) ABSTRACT

The present invention has an object to provide a curable composition for transfer materials. The curable composition is applicable to a UV nanoimprint process capable of forming micropatterns with high throughput, is applicable to a thermal nanoimprint process in some cases, and is capable of forming a micropattern having high selectivity on etching rates regarding a fluorine-based gas and an oxygen gas. A curable composition for transfer materials of the present invention contains a curable silicon compound produced by subjecting a silicon compound (A) having a Si—H group and a compound (B) having a curable functional group and a carbon-carbon double bond other than the curable functional group to a hydrosilylation reaction.

2 Claims, 7 Drawing Sheets

EPOXY GROUP-CONTAINING ORGANOSILOXANE COMPOUND, CURABLE COMPOSITION FOR TRANSFER MATERIALS AND METHOD FOR FORMING MICROPATTERN USING THE COMPOSITION

CROSS REFERENCE TO RELATED APPLICATIONS

This application is a National Stage of International Application No. PCT/JP2008/070122 filed Nov. 5, 2008, the contents of which are incorporated herein by reference in their entirety.

TECHNICAL FIELD

The present invention relates to a novel epoxy group-containing organosiloxane compound; a curable composition for transfer materials which is suitable for use in forming a micropattern by an imprinting process; and a method for forming a micropattern using the curable composition.

BACKGROUND ART

Nanoimprint techniques have been attracting attention as micropattern-forming methods usable in semiconductor fabrication processes and processes for manufacturing magnetic recording media such as patterned media. Excellent transfer materials suitable for use in it are required.

Thermoplastic resins such as poly(methyl methacrylate) are used as transfer materials for nanoimprinting in some cases. In such cases, the following cycle is usually used: a cycle in which a coated material is heated to a temperature higher than or equal to the glass transition temperature thereof, pressed with a die, cooled, and then the die is removed. There is a problem in such a method that it takes a very long time and therefore has low throughput.

Japanese Unexamined Patent Application Publication No. 2003-100609 discloses a technique for forming a micropattern in such a manner that a coated film is formed on a substrate using a solution-processing material containing a solvent and a hydrogenated silsesquioxane which is one of siloxane compounds and is then pressed with a die at room temperature, the solvent is removed, and a hydrolytic curing is carried out. Japanese Unexamined Patent Application Publication No. 2005-277280 discloses a technique for obtaining a micropattern in such a manner that a coated film is formed on a substrate by a composition comprising a catechol derivative and a resorcinol derivative and is then pressed with a die at room temperature.

These techniques, which are called room-temperature imprinting techniques, can omit heating-cooling cycles. However, these techniques require a long time for pressing with a die and therefore have insufficient throughput. Stampers are pressed with a high pressure and therefore have a drawback in lifetime; hence, these techniques cannot be said to be sufficient as mass-production techniques as well.

A technique, called UV nanoimprinting, using a photocurable resin curable by an ultraviolet ray has been proposed. In this process, a micropattern is formed in such a manner that after the photocurable resin is coated, the resin is cured by irradiation with an ultraviolet ray while pressing the resin with a stamper, and the stamper is then removed therefrom. This process includes no heating-cooling cycle. The curing by the ultraviolet ray can be completed in a very short time. The force applied for the pressing with the stamper is small. It is likely that the process can solve the above various problems.

In UV nanoimprinting an organic resin such as an acrylic resin is usually used. In the case of using a micropattern formed therefrom as a resist, selectivity on etching rates regarding the types of etching gases is important. The term "selectivity on etching rates" as used herein means that the rate of etching varies depending on the types of etching gases. The fact that the etching rate varies significantly means that selectivity etching rates is high.

In the case where the micropattern functions as a resist, the micropattern needs to have high resistance to an etching gas and also needs to be readily removed by a gas used for the removal when removed. That is, the micropattern needs to have high selectivity on etching rates. Examples of gases often used as etching gases include fluorine-based gases and an oxygen gas. Resins generally do not have significant differences in etching rates of the fluorine-based gases and the oxygen gas. In order to increase selectivity on etching rates of fluorine-based gases and the oxygen gas, a silicon compound is usually used. The aforementioned hydrogenated silsesquioxane is an example of the silicon compound and is characteristic in that the hydrogenated silsesquioxane is etched with the fluorine-based gases at a high rate but is etched with an oxygen gas at a very low rate. However, the hydrogenated silsesquioxane is not photocurable and therefore has a problem of being applicable to UV nanoimprint process.

As a method solving the problem, Japanese Unexamined Patent Application Publication No. 2007-72374 discloses a process which uses a silicon compound synthesized by a sol-gel process and has a functional group. This technique is useful in solving the above problem. However, in this technique, the molecular weight of the silicon compound cannot be increased because the increase of the molecular weight of the silicon compound by the sol-gel process causes the compound to be gelled to become a compound insoluble in any solvent. Therefore, the process suggested in Japanese Unexamined Patent Application Publication No. 2007-72374 has a problem that it is difficult to balance the strength and flexibility of a micropattern during and after the imprint molding.

Patent Document 1: Japanese Unexamined Patent Application Publication No. 2003-100609
Patent Document 2: Japanese Unexamined Patent Application Publication No. 2005-277280
Patent Document 3: Japanese Unexamined Patent Application Publication No. 2007-72374

DISCLOSURE OF INVENTION

Problems to be Solved by the Invention

The present invention has an object to provide a curable composition for transfer materials having the following three properties:
(1) the applicability to a UV nanoimprint process capable of forming micropatterns with high throughput,
(2) the applicability to a thermal nanoimprint process in some cases, and
(3) the capability of forming a micropattern having high selectivity on etching rates regarding fluorine-based gases and an oxygen gas.

Means for Solving the Problems

The inventors have made intensive studies to solve the above problems. As a result, the inventors have found that the problems can be solved by introducing a curable functional group to a silicon compound having a Si—H group. That is, the inventors have found that the following can solve the above problems:

(1) a curable composition containing a compound produced by adding a compound having a curable functional group and a carbon-carbon double bond other than the curable functional group to the Si—H group-having silicon compound by a hydrosilylation reaction and (2) a curable composition containing the compound and a compound which reacts with the curable functional group in combination.

The inventors have invented a novel compound during the studies. The novel compound can be used as a component of, for example, the above curable compositions (usable as transfer materials).

Specifically, the essentials of the present invention are as set forth in the following Items [1] to [11] below.

[1] An epoxy group-containing organosiloxane compound represented by the following formula (1), (2), or (3) below.

[Chem. 1]

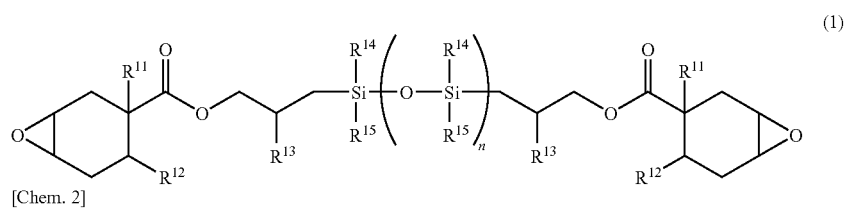

(1)

[Chem. 2]

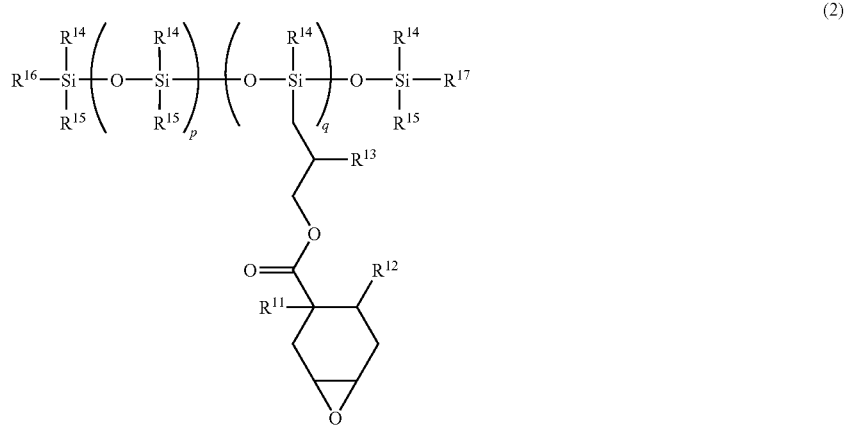

(2)

[Chem. 3]

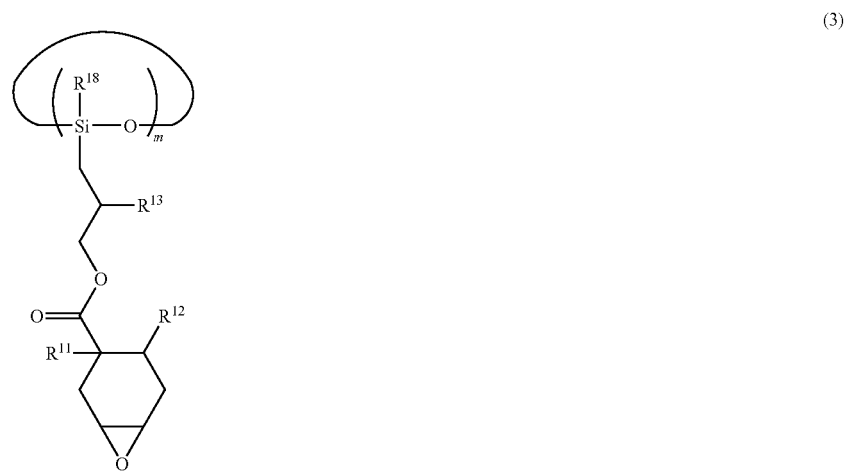

(3)

wherein $R^{11}$ is a hydrogen atom or a methyl group; $R^{12}$ is a hydrogen atom, a methyl group or a phenyl group; $R^{13}$ is a hydrogen atom or a methyl group; $R^{14}$ and $R^{15}$ are independently a substituted or unsubstituted monovalent hydrocarbon group having 1 to 10 carbon atoms; $R^{16}$ and $R^{17}$ are independently a substituted or unsubstituted monovalent hydrocarbon group having 1 to 10 carbon atoms or a monovalent hydrocarbon group represented by the following general formula (4); n and q are each an integer of one or more; $R^{18}$ is a hydrogen atom, a methyl group, an ethyl group or a phenyl group; p is an integer of zero or more; and m is an integer of 3 to 6.

[Chem. 4]

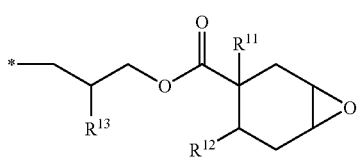

(4)

wherein $R^{11}$ is a hydrogen atom or a methyl group; $R^{12}$ is a hydrogen atom, a methyl group or a phenyl group; $R^{13}$ is a hydrogen atom or a methyl group; and * represents a bond.

[2] A curable composition for transfer materials containing a curable silicon compound produced by subjecting a silicon compound (A) having a Si—H group and a compound (B) having a curable functional group and a carbon-carbon double bond other than the curable functional group to a hydrosilylation reaction.

[3] The curable composition for transfer materials as described in Item [2], wherein the compound (A) is at least one selected from the group consisting of a cyclic siloxane compound and a linear siloxane compound.

[4] The curable composition for transfer materials as described in Item [2] or [3], wherein the curable functional group is an energy ray-curable functional group.

[5] The curable composition for transfer materials as described in Item [4], wherein the energy ray-curable functional group is at least one selected from the group consisting of a (meth)acrylic group and an epoxy group.

[6] The curable composition for transfer materials as described in any one of Items [2] to [5], wherein the compound (B) is at least one of compounds represented by the following formulas (a) to (d).

[Chem. 5]

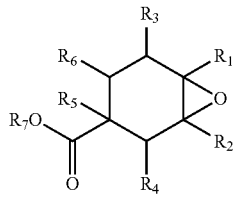

(a)

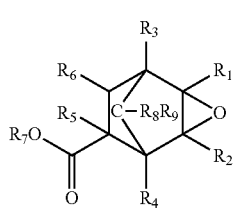

(b)

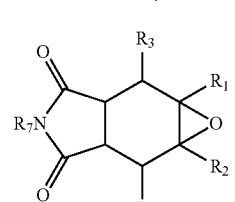

(c)

-continued

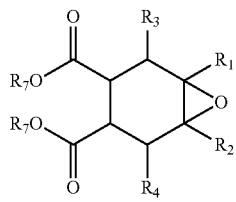

(d)

wherein $R_1$ to $R_5$, $R_8$ and $R_9$ are each independently hydrogen or a methyl group; $R_6$ is hydrogen, a methyl group or a phenyl group; and $R_7$ is an allyl group, a 2-methyl-2-propenyl group, a 3-butenyl group or a 4-pentenyl group.

[7] The curable composition for transfer materials as described in any one of Items [2] to [6], wherein the composition further contains an acid anhydride and the compound (B) contains at least one selected from the group consisting of a glycidyl group and a cyclohexene oxide group.

[8] A method for forming a micropattern with a size of 10 μm or less, comprising a step of applying the curable composition for transfer materials as described in any one of Items [4] to [6] to a substrate, a step of pressing a die to the curable composition for transfer materials, a step of curing the curable composition for transfer materials by energy ray irradiation, and a step of removing the die from the cured curable composition for transfer materials.

[9] A method for forming a micropattern with a size of 10 μm or less, comprising a step of applying the curable composition for transfer materials as described in any one of Items [2] to [7] to a substrate, a step of pressing a die to the curable composition for transfer materials, a step of curing the curable composition for transfer materials by heating, and a step of removing the die from the cured curable composition for transfer materials.

[10] The method for forming a micropattern with a size of 10 μm or less as described in Item [8], wherein the step of curing the curable composition for transfer materials is performed by heating and energy ray irradiation.

[11] The method for forming a micropattern with a size of 10 μm or less as described in Item [8] or [10], wherein the die is made of resin, glass or quartz and the step of curing the curable composition for transfer materials is performed by irradiating the energy ray in a direction from the die to the substrate.

Advantages of the Invention

The present invention can provide a curable composition for transfer materials which is useful in forming a micropattern having high throughput and high selectivity on etching rates regarding fluorine-based gases and an oxygen gas. The curable composition for transfer materials is suitable for use in a method for forming such micropattern. Furthermore, the present invention can provide a novel compound usable as a component of the curable composition for transfer materials.

EXPLANATION OF REFERENCE

Figure 1:
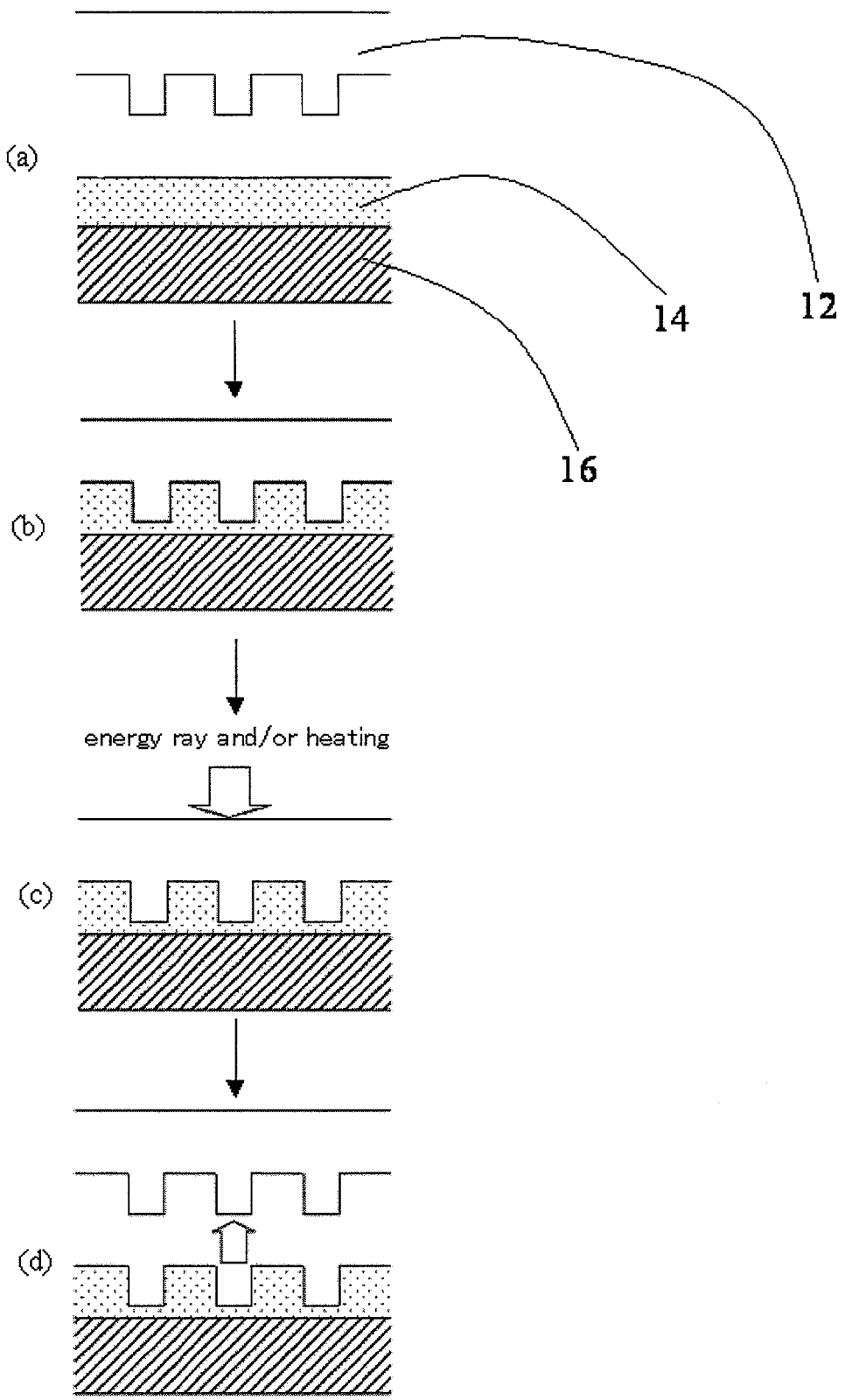
FIG. 1 is a chart showing steps of a method for forming a micropattern with a size of 10 μm or less using a curable composition for transfer materials according to the present invention.

| 12 | die |
|----|-----|
| 14 | coated film of a curable composition for transfer materials according to the present invention |
| 16 | substrate |

BEST MODES FOR CARRYING OUT THE INVENTION

A curable composition for transfer materials according to the present invention and a method for forming a micropattern using the curable composition will be described in detail. In advance of that, a novel compound invented by the present inventors is described.

[Epoxy Group-Containing Organosiloxane Compound]

The novel compound invented by the present inventors is an epoxy group-containing organosiloxane compound represented by the following general formula (1), (2) or (3).

[Chem. 6]

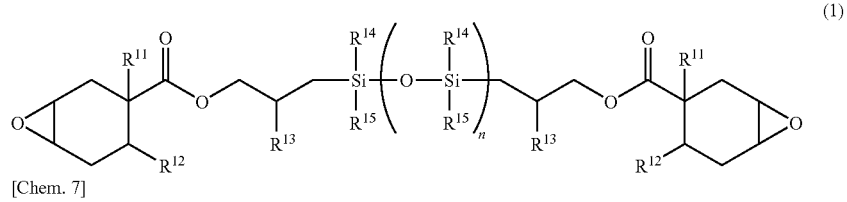

(1)

[Chem. 7]

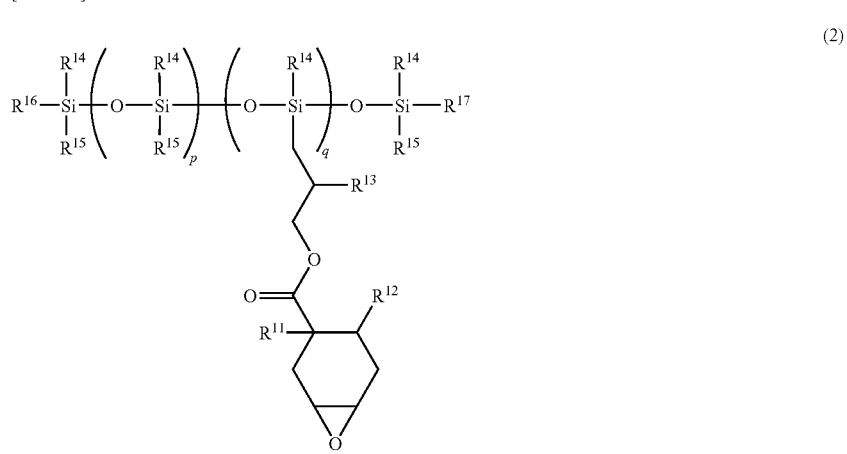

(2)

[Chem. 8]

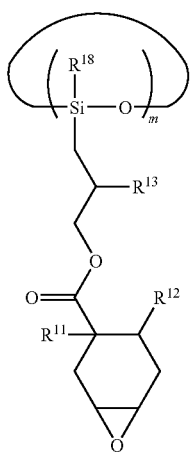

(3)

In the above formulas (1) to (3), $R^{11}$ is a hydrogen atom or a methyl group; $R^{12}$ is a hydrogen atom, a methyl group or a phenyl group; $R^{13}$ is a hydrogen atom or a methyl group; $R^{14}$ and $R^{15}$ are independently a substituted or unsubstituted monovalent hydrocarbon group having 1 to 10 carbon atoms; $R^{16}$ and $R^{17}$ are independently a substituted or unsubstituted monovalent hydrocarbon group having 1 to 10 carbon atoms or a monovalent hydrocarbon group represented by the following general formula (4) below; $R^{18}$ is a hydrogen atom, a methyl group, an ethyl group or a phenyl group; n and q are each an integer of 1 or more; p is an integer of 0 or more; and m is an integer of 3 to 6.

[Chem. 9]

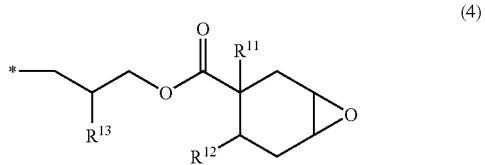

(4)

In the above formula (4), $R^{11}$ is a hydrogen atom or a methyl group; $R^{12}$ is a hydrogen atom, a methyl group, or a phenyl group; $R^{13}$ is a hydrogen atom or a methyl group; and * represents a bond.

A substituent group in the substituted or unsubstituted monovalent hydrocarbon group having 1 to 10 carbon atoms is an alkyl group having 1 to 10 carbon atoms or an aryl group. Examples thereof include a methyl group, an ethyl group, a n-propyl group, an isopropyl group, a n-butyl group, a sec-butyl group, an isobutyl group, a t-butyl group, a n-pentyl group, a cyclopentyl group, a n-hexyl group, a cyclohexyl group, a n-octyl group, a benzyl group, a 2-phenylethyl group, a 3-phenylpropyl group, a phenyl group, a p-t-butylphenyl group, a p-tolyl group, an o-tolyl group, a 1-naphthyl group and a 2-naphthyl group.

The substituted or unsubstituted monovalent hydrocarbon group having 1 to 10 carbon atoms preferable as $R^{14}$ and $R^{15}$ is a methyl group, an ethyl group, a n-propyl group or a phenyl group.

The substituted or unsubstituted monovalent hydrocarbon group having 1 to 10 carbon atoms preferable as $R^{16}$ and $R^{17}$ is a methyl group, an ethyl group or a phenyl group.

In addition, n is an integer of 1 or more and is preferably an integer of 1 to 50 and more preferably 1 to 5.

q is an integer of 1 or more and is preferably an integer of 1 to 30 and more preferably 2 to 10.

p is an integer of 0 or more and is preferably an integer of 0 to 200 and more preferably 1 to 100.

m is an integer of 3 to 6 and is preferably an integer of 4 to 5.

The epoxy group-containing organosiloxane compound according to the present invention can be used as, for example, a curable silicon compound in the curable composition for transfer materials according to the present invention described below.

Regarding a method for producing the epoxy group-containing organosiloxane compound according to the present invention, the production process is the same as a process for producing the curable silicon compound (in which the epoxy group-containing organosiloxane compound according to the present invention is included) in the curable composition for transfer materials according to the present invention described below, and therefore the explanation thereof is omitted here.

[Curable Composition for Transfer Materials]

The curable composition for transfer materials according to the present invention (hereinafter also simply referred to as "curable composition") contains the curable silicon compound which is produced by subjecting a silicon compound (hereinafter also simply referred to as "Compound (A)") having a Si—H group and a compound (hereinafter also simply referred to as "Compound (B)") having a curable functional group and a carbon-carbon double bond other than the curable functional group to a hydrosilylation reaction.

<Si—H Group-Having Silicon Compound (Compound (A))>

Examples of the Compound (A) include cyclic siloxane compounds such as 1,3,5,7-tetramethylcyclotetrasiloxane, 1,3,5,7-tetraethylcyclotetrasiloxane, 1,3,5,7-tetraphenylcyclotetrasiloxane, 1,3,5,7,9-pentamethylcyclopentasiloxane and 1,3,5,7,9-pentaphenylcyclopentasiloxane; and linear siloxane compounds such as 1,1,3,3,-tetramethyldisiloxane, 1,1,3,3,5,5-hexamethyltrisiloxane, polydimethylsiloxanes both ends of which are hydrogenated, methyl hydrogen polysiloxanes and methyl hydrogen siloxane-dimethyl siloxane copolymers.

Silane compounds such as dialkylsilanes, monoalkylsilanes, diphenylsilanes and phenylsilanes can be used as Compound (A).

Among them, cyclic or linear siloxane compounds having 3 or more Si—H groups are preferred in view of the curability of curable compositions obtained therefrom. Specifically, 1,3,5,7-tetramethylcyclotetrasiloxane and 1,3,5,7,9-pentamethylcyclopentasiloxane are preferred.

The Compound (A) may be used alone or in combination of 2 or more kinds thereof.

<Compound Having a Curable Functional Group and a Carbon-Carbon Double Bond Other than the Curable Functional Group (Compound (B))>

The curable functional group in the Compound (B) is herein defined as a functional group capable of causing a curing reaction by heat or an energy ray in the presence or absence of a polymerization initiator (a heat-curable or energy ray-curable functional group) or a functional group capable of reacting with another functional group to be cured.

Examples of the heat-curable functional group include an acrylic group, a methacrylic group, an epoxy group, a styryl group, a vinyl group, an amino group, a thiol group and an isocyanate group.

Examples of the energy ray-curable functional group include an acrylic group, a methacrylic group, an epoxy group, a styryl group and a vinyl group. These functional groups are also heat-curable.

The term "epoxy group" as used herein means a group having a structure in which two carbon atoms directly bonded to each other or indirectly bonded to each other through another atom (principally a carbon atom) are bridged by an oxygen atom as well as a group having a triangular structure which is used in its usual meaning and in which two carbon atoms directly bonded to each other are bridged by an oxygen atom. Therefore, the term "epoxy group" as used herein covers a glycidyl group, an oxetanyl group, a cyclohexene oxide group and the like.

The above curable functional group is preferably a (meth)acrylic group or an epoxy group in view of the curing rate of resulting curable compositions.

Next, the carbon-carbon double bond in the Compound (B) is described. The carbon-carbon double bond is necessary to carry out the hydrosilylation reaction. Examples of the carbon-carbon double bond include a vinyl group, an allyl group, an isopropenyl group, a 2-methyl-2-propenyl group, a 3-butenyl group and a 4-pentenyl group.

Examples of the compound containing the curable functional group and the carbon-carbon double bond other than the curable functional group in a molecule include compounds having an epoxy group and an allyl group such as allyl glycidyl ether, 1,2-epoxy-4-vinylcyclohexane and allyl 3,4-epoxycyclohexanecarboxylate, compounds having an acrylic or methacrylic group and an allyl group such as allyl acrylate, allyl methacrylate, ethylene glycol monoallyl ether acrylate, ethylene glycol monoallyl ether methacrylate, propylene glycol monoallyl ether acrylate and propylene glycol monoallyl ether methacrylate, compounds having a sulfide group and an allyl group such as allyl sulfide, and compounds having an amino group and an allyl group such as allyl amine.

The examples include compounds having a cyclohexene oxide group which has high activity for cationic polymerization and an allyl group, 2-methyl-2-propenyl group or vinyl group which has high activity for hydrosilylation reaction. The following compounds having structures below are preferred in view of the curing rate of the obtained curable compositions.

[Chem. 10]

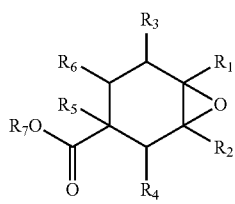
(a)

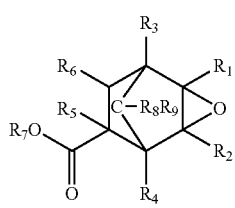
(b)

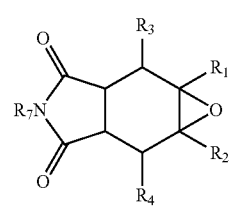
(c)

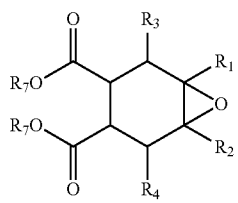
(d)

In the above formulas, $R_1$ to $R_5$, $R_8$ and $R_9$ are each independently hydrogen or a methyl group; $R_6$ is hydrogen, a methyl group or a phenyl group; and $R_7$ is an allyl group, a 2-methyl-2-propenyl group, a 3-butenyl group or a 4-pentenyl group.

The Compound (B) may be used alone or in combination of two or more kinds thereof.

<Curable Silicon Compound>

The curable silicon compound which constitutes the curable composition for transfer materials according to the present invention is produced by subjecting the above Compound (A) and Compound (B) to the hydrosilylation reaction. A general hydrosilylation reaction is depicted below.

[Chem. 11]

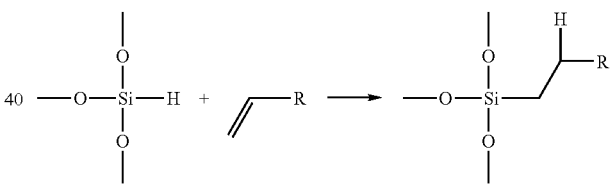

When Compound (A) is, for example, 1,3,5,7-tetramethyltetrasiloxane (see Formula (I) below) and Compound (B) is, for example, allyl 3,4-epoxycyclohexanecarboxylate (see Formula (II) below), a compound (see Formula (III) below) having a structure below is mainly produced by the hydrosilylation reaction.

[Chem. 12]

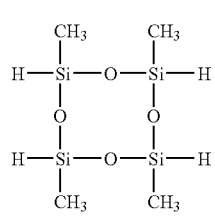
(I)

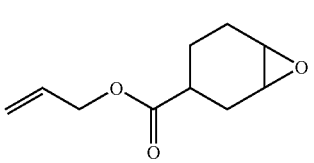
(II)

[Chem. 13]

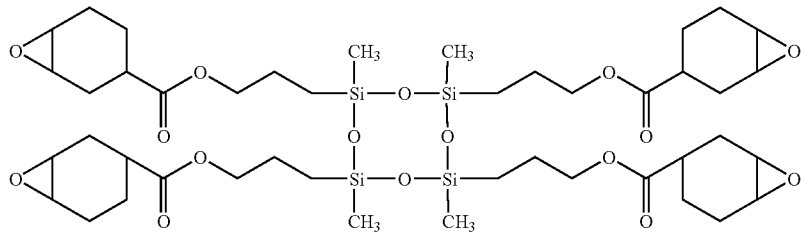

(III)

As described above, by subjecting the Compound (A) and Compound (B) to the hydrosilylation reaction, the curable silicon compound having a heat-curable functional group and/or an energy ray-curable functional group is produced. The ratio of the Compound (A) to the Compound (B) used is set such that the ratio of the number of carbon-carbon double bonds to that of Si—H groups (carbon-carbon double bond/Si—H group ratio) is usually 0.8 or more and preferably 0.98 to 1.5. When the ratio is less than 0.8, other side reactions are likely to be caused due to the remaining Si—H groups. When an excessive amount of the Compound (B) which has the carbon-carbon double bonds is used, that is, when the ratio is excessively large, a large amount of the Compound (B) remains and therefore additional operations such as distillation and purification are necessary in a certain case.

A catalyst is used in the hydrosilylation reaction and is preferably a platinum catalyst. Examples thereof include chloroplatinic acid, platinum-olefin complexes, platinum vinyl group-containing siloxane complexes and platinum carbonyl complexes.

The amount of the catalyst added should be an effective amount to carry out the reaction and is specifically such that the amount of platinum contained in the catalyst is 0.01 to 10,000 ppm and preferably 0.1 to 5,000 ppm with respect to the sum of the amount of the Compound (A) and that of the Compound (B) on a weight basis.

The temperature of the reaction is not particularly limited as long as the reaction proceeds. The reaction can be usually carried out at 0° C. to 250° C. The reaction is carried out preferably with heating to 50° C. or higher because the reaction proceeds quickly. On the other hand, when the reaction temperature is higher than 150° C., many side reactions occur; hence, the reaction is carried out preferably at 150° C. or lower and more preferably at 100° C. or lower. The time of the reaction is not particularly limited and is preferably 1 to 20 hours.

Since the Compound (A) and the platinum catalyst are sensitive to moisture, the reaction may be carried out in an argon or nitrogen atmosphere as required.

The use of the curable composition for transfer materials, which contains the curable silicon compound obtained as described above, according to the present invention allows a micropattern with a size of 10 μm or less to be formed with high throughput by a UV nanoimprint process. The obtained micropattern has high selectivity on etching rates of a fluorine-based gas and an oxygen gas.

In the case of forming the micropattern using the curable composition according to the present invention, components below may be contained therein if necessary.

<Solvent>

The curable composition according to the present invention may contain a solvent for the purpose of enhancing coating properties. Examples of the solvent include ketone solvents such as methyl isobutyl ketone;

aromatic hydrocarbon solvents such as toluene and xylene; ether solvents such as diethyl ether;

ester solvents such as ethyl acetate, butyl acetate and propylene glycol monomethyl ether acetate;

alcohol solvents such as 2-propanol, butanol and hexanol; and halogenated hydrocarbon solvents such as chloroform, trichloroethylene and carbon tetrachloride.

<Photopolymerization Initiator>

When the curable composition according to the present invention is energy ray-curable, the curable composition contains a photopolymerization initiator if necessary. The presence of the photopolymerization initiator therein increases the curing rate of the curable composition.

An energy ray used for an energy ray curing is not particularly limited as long as it acts on the curable functional group in the curable silicon compound described above to cure the curable composition according to the present invention. Examples of the energy ray include radiations such as ultraviolet rays and X-rays and electron beams. In particular, an ultraviolet ray and an X-ray are preferred in view of the cost and safety of an apparatus for generating the energy ray.

The photopolymerization initiator is selected depending on the curable functional group in the curable silicon compound.

When the curable functional group is a (meth)acryloyl group, a vinyl group or an allyl group, the following initiator is selected: an acetophenone photoradical polymerization initiator such as 4-phenoxydichloroacetophenone, 4-t-butyldichloroacetophenone, 4-t-butyl-trichloroacetophenone, diethoxyacetophenone, 2-hydroxy-2-cyclohexylacetophenone, 2-hydroxy-2-phenyl-1-phenylpropane-1-one, 1-(4-dodecylphenyl)-2-hydroxy-2-methylpropane-1-one, 1-(4-isopropylphenyl)-2-hydroxy-2-methylpropane-1-one, 4-(2-hydroxyethoxy)-phenyl-(2-hydroxy-2-propyl) ketone, 1-hydroxycyclohexyl phenyl ketone or 2-methyl-1-[4-(methylthio)phenyl]-2-morpholinopropane-1;

a benzoin photoradical polymerization initiator such as benzoin, benzoin methyl ether, benzoin isopropyl ether, benzoin isobutyl ether or benzyl methyl ketal;

a benzophenone photoradical polymerization initiator such as benzophenone, benzoylbenzoic acid, methyl benzoylbenzoate, 4-phenylbenzophenone, hydroxybenzophenone, an acrylated benzophenone, 4-benzoil-4'-methyldiphenyl sulfide, 3,3'-dimethyl-4-methoxybenzophenone, 4,4'-dimethylaminobenzophenone, 4,4'-diethylaminobenzophenone or 3,3',4,4'-tetra(t-butylperoxycarbonyl)benzophenone;

a thioxanthone photoradical polymerization initiator such as thioxanthone, 2-chlorothioxanthone, 2-methylthioxanthone, 2,4-dimethylthioxanthone, 2,4-diethylthioxanthone, 2,4-diisopropylthioxanthone, isopropylthioxanthone, 1-chloro-4-propoxythioxanthone or 2,4-dichlorothioxanthone;
a ketone photoradical polymerization initiator such as an α-acyloxime ester, methyl phenylglyoxylate, benzyl, 9,10-phenanthrenequinone, camphorquinone, dibenzosuberone, 2-ethylanthraquinone or 4',4''-diethylisophthalophenone;
an imidazole photoradical polymerization initiator such as 2,2'-bis(2-chlorophenyl)-4,4',5,5'-tetraphenyl-1,2'-imidazole;
an acylphosphine oxide photoradical polymerization initiator such as 2,4,6-trimethylbenzoyldiphenylphosphine oxide;
a carbazole photoradical polymerization initiator; or
a photoradical polymerization initiator represented by an onium salt of a Lewis acid such as triphenylphosphonium hexafluoroantimonate, triphenylphosphonium hexafluorophosphate, p-(phenylthio)phenyldiphenylsulfonium hexafluoroantimonate, 4-chlorophenyldiphenylsulfonium hexafluorophosphate or (2,4-cyclopentadiene-1-yl)[(1-methylethyl)benzene]-iron-hexafluorophosphate.

When the curable functional group is an epoxy group, the following initiator is selected: a cationic photopolymerization initiator such as a sulfonium salt including triphenylsulfonium hexafluoroantimonate, an iodonium salt, a diazonium salt or an allene-ion complex.

These photopolymerization initiators may be used alone or in combination of two or more kinds thereof. The amount of the photopolymerization initiator contained in the curable composition is preferably 0.01 to 10 parts by mass based on 100 parts by mass of a solid component of the curable composition, that is, the curable silicon compound.

<Thermal Polymerization Initiator>

There are two processes for curing the curable functional group: heat curing and energy ray curing.

When the curable composition according to the present invention is heat-curable, a thermal polymerization initiator is contained therein if necessary. The presence of the thermal polymerization initiator therein increases the curing rate of the curable composition.

The thermal polymerization initiator is selected depending on the curable functional group in the curable silicon compound. When the curable functional group is a (meth)acryloyl group, a vinyl group or an allyl group, the following initiator is selected: an organic hydroperoxide such as methyl ethyl ketone peroxide, cyclohexanone peroxide, methylcyclohexanone peroxide, methyl acetate peroxide, acetyl acetate peroxide, 1,1-bis(t-butylperoxy)butane, 1,1-bis(t-butylperoxy)cyclohexane, 1,1-bis(t-butylperoxy)-2-methylcyclohexane, 1,1-bis(t-butylperoxy)-3,3,5-trimethylcyclohexane, 1,1-bis(t-butylperoxy)cyclododecane, 1,1-bis(t-hexylperoxy)cyclohexane, 1,1-bis(t-hexylperoxy)-3,3,5-trimethylcyclohexane, 2,2-bis(4,4-di-t-butylperoxycyclohexyl) propane, t-butyl hydroperoxide, t-hexyl hydroperoxide, 1,1,3,3-tetramethylbutyl hydroperoxide, cumene hydroperoxide, p-methyl hydroperoxide, diisopropylbenzene hydroperoxide, di-t-butyl peroxide, dicumyl peroxide, t-butylcumyl peroxide, α,α'-bis(t-butylperoxy)diisopropylbenzene, 2,5-dimethyl-2,5-bis(t-butylperoxy)hexane, 2,5-dimethyl-2,5-bis(t-butylperoxy)hexyne-3, isobutyryl peroxide, 3,3,5-trimethylhexanoyl peroxide, octanoyl peroxide, lauroyl peroxide, stearoyl peroxide, succinic peroxide, m-toloylbenzoyl peroxide, benzoyl peroxide, di-n-propyl peroxydicarbonate, diisopropyl peroxydicarbonate, bis(4-t-butylcyclohexyl) peroxydicarbonate, di-2-ethoxyethyl peroxydicarbonate, di-2-ethoxyhexyl peroxydicarbonate, di-3-methoxybutyl peroxydicarbonate, di-S-butyl peroxydicarbonate, di(3-methyl-3-methoxybutyl) peroxydicarbonate, α,α'-bis(neodecanoylperoxy)diisopropylbenzene, t-butyl peroxyneodecanoate, t-hexyl peroxyneodecanoate, 1,1,3,3-tetramethylbutyl peroxyneodecanoate, 1-cyclohexyl-1-methylethyl peroxyneodecanoate, cumyl peroxyneodecanoate, t-butyl peroxypivalate, t-hexyl peroxypivalate, t-butyl peroxy-2-ethylhexanoate, t-hexyl peroxy-2-ethylhexanoate, 1,1,3,3-tetramethylbutyl peroxy-2-ethylhexanoate, 2,5-dimethyl-2,5-bis(2-ethylhexanoylperoxy)hexane, 1-cyclohexyl-1-methylethyl peroxy-2-ethylhexanoate, t-butyl peroxy-3,5,5-trimethylhexanoate, t-butylperoxyisopropyl monocarbonate, t-hexylperoxyisopropyl monocarbonate, t-butylperoxy-2-ethylhexyl monocarbonate, t-butylperoxyallyl monocarbonate, t-butyl peroxyisobutyrate, t-butyl peroxymaleate, t-butyl peroxybenzoate, t-hexyl peroxybenzoate, t-butyl peroxy-m-toluoylbenzoate, t-butyl peroxylaurate, t-butyl peroxyacetate, bis(t-butylperoxy)isophthalate, 2,5-dimethyl-2,5-bis(m-toluoylperoxy)hexane, 2,5-dimethyl-2,5-bis(benzoylperoxy)hexane, t-butyl trimethylsilyl peroxide, 3,3',4,4'-tetra(t-butylperoxycarbonyl)benzophenone or 2,3-dimethyl-2,3-diphenylbutane or
a thermal photoradical polymerization initiator represented by an azo compound such as 1-[(1-cyano-1-methylethyl)azo]formamide, 1,1'-azobis(cyclohexane-1-carbononitrile), 2,2'-azobis(2-methylbutyronitrile), 2,2'-azobisisobutyronitrile, 2,2'-azobis(2,4-dimethyl-4-methoxyvaleronitrile), 2,2'-azobis(2,4-dimethylvaleronitrile), 2-phenylazo-4-methoxy-2,4-dimethylvaleronitrile, 2,2'-azobis(2-methylpropionamidine) dihydrochloride, 2,2'-azobis(2-methyl-N-phenylpropionamidine)dihydrochloride, 2,2'-azobis[N-(4-chlorophenyl)-2-methylpropionamidine] dihydrochloride, 2,2'-azobis[N-(4-hydrophenyl)-2-methylpropionamidine]dihydrochloride, 2,2'-azobis[2-methyl-N-(2-propenyl)propionamidine]dihydrochloride, 2,2'-azobis[N-(2-hydroxyethyl)-2-methylpropionamidine]dihydrochloride, 2,2'-azobis[2-methyl-N-(phenylmethyl) propionamidine]dihydrochloride, 2,2'-azobis[2-(2-imidazoline-2-yl)propane]dihydrochloride, 2,2'-azobis[2-(2-imidazoline-2-yl)propane]dihydrochloride, 2,2'-azobis[2-(5-methyl-2-imidazoline-2-yl)propane] dihydrochloride, 2,2'-azobis{2-[1-(2-hydroxyethyl)-2-imidazoline-2-yl]propane}dihydrochloride, 2,2'-azobis[2-(4,5,6,7-tetrahydro-1H-1,3-diazepine-2-yl)propane] dihydrochloride, 2,2'-azobis[2-(3,4,5,6-tetrahydropyrimidine-2-yl)propane]dihydrochloride, 2,2'-azobis[2-(5-hydroxy-3,4,5,6-tetrahydropyrimidine-2-yl)propane]dihydrochloride, 2,2'-azobis(2-methylpropionamide), 2,2'-azobis[2-methyl-N-(2-hydroxyethyl)propionamide], 2,2'-azobis{2-methyl-N-[1,1-bis(hydroxymethyl)-2-hydroxyethyl]propionamide}, 2,2'-azobis{2-methyl-N-[1,1-bis(hydroxymethyl)ethyl] propionamide}, 2,2'-azobis(2-methylpropane), 2,2'-azobis (2,4,4-trimethylpentane), dimethyl 2,2'-azobis(2-methylpropionate), 4,4'-azobis(4-cyanopentanoic acid) or 2,2'-azobis[2-(hydroxymethyl)propionitrile].

When the curable functional group is an epoxy group, the following compounds are selected: imidazoles such as melamine, imidazole, 2-methylimidazole, 2-undecylimidazole, 2-heptacylimidazole, 2-ethyl-4-ethylimidazole, 2-phenylimidazole, 2-phenyl-4-methylimidazole, 1-benzyl-2-methylimidazole, 1-benzyl-2-phenylimidazole, 1,2-dimethylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-cyanoethyl-2-undecylimidazolium trimellitate, 1-cyanoethyl-2- phenylimidazolium trimellitate, 2,4-diamino-6-[2'-methylimidazolyl-(1')]-ethyl-S-triazine, 2,4-diamino-6-[2'-undecylimidazolyl-(1')]-ethyl-S-triazine, 2,4-diamino-6-[2'-ethyl-4'-imidazolyl-(1')]-ethyl-S-triazine, 2,4-diamino-6-[2'-methylimidazolyl-(1')]-ethyl-S-triazine isocyanuric acid adduct, 2-phenylimidazole isocyanuric acid adduct, 2-methylimidazole isocyanuric acid adduct, 2-phenyl-4,5-dihydroxymethylimidazole, 2-phenyl-4-methyl-5-hydroxymethylimidazole, 2,3-dihydro-1H-pyrrolo[1,2-a]benzimidazole, 4,4'-methylenebis(2-ethyl-5-methylimidazole), and 1-dodecyl-2-methyl-3-benzylimidazolium chloride;

strong organic bases and salts thereof such as 1,8-diazabicyclo(5,4,0)undecene-7 and phenol, octyl, p-toluene sulfonic acid, formic acid, orthophthalic acid or phenol-novolak resin salt thereof, or 1,5-diazabicyclo(4,3,0)nonene-5 and its phenol-novolak resin salt;

anionic initiators represented by quaternary phosphonium bromides and ureas such as aromatic dimethylureas and aliphatic dimethylureas;

cationic silanol catalysts such as triphenylsilanol; and aluminum chelate catalysts such as aluminum tris(acetylacetone).

These thermal polymerization initiators may be used alone or in combination of two or more kinds thereof. The amount of the thermal polymerization initiator contained in the curable composition is preferably 0.01 to 10 parts by mass with respect to 100 parts by mass of a solid component of the curable composition, that is, the curable silicon compound.

When the Compound (B) has at least one group selected from the group consisting of a glycidyl group and a cyclohexene oxide group, an acid anhydride compound serving as a curing agent may be contained in the curable composition according to the present invention such that the composition is cured by energy ray irradiation.

Examples of the acid anhydride compound include aromatic acid anhydrides such as phthalic anhydride, trimellitic anhydride and pyromellitic anhydride and cyclic aliphatic anhydrides such as tetrahydrophthalic anhydride, methyltetrahydrophthalic anhydride, hexahydrophthalic anhydride and methylhexahydrophthalic anhydride.

The amount of the acid anhydride compound used is usually 0.7 to 1.2 equivalents and preferably 0.8 to 1.1 equivalents with respect to the glycidyl or cyclohexene oxide group.

Furthermore, a curing accelerator such as an imidazole, tertiary amine, or organic phosphine compound may be contained in the curable composition according to the present invention.

The curable composition according to the present invention may contain an additive such as a viscosity modifier, a dispersant and a surface conditioner in addition to the aforementioned polymerization initiator, the curing agent and the curing accelerator. The amount of the total additives used is preferably not more than 30 parts by mass based on 100 parts by mass of the curable composition for transfer materials. When the amount of the additives used is excessively large, the micropattern which is obtained using the curable composition for transfer materials according to the present invention is likely to have poor etching performance.

[Method for forming micropattern with a size of 10 μm or less]

A method for forming a micropattern with a size of 10 μm or less using the curable composition for transfer materials according to the present invention is described below. The term "micropattern with a size of 10 μm or less" as used herein means a pattern formed in a die having concave and convex lines with a width of 10 μm or less, that is, a pattern in which the sum of the width of the concave line and that of the convex line is 10 μm or less.

The method for forming a micropattern with a size of 10 μm or less according to the present invention comprises a step of applying the curable composition for transfer materials according to the present invention to a substrate, a step of pressing a die to the curable composition for transfer materials, a step of curing the curable composition for transfer materials by energy ray irradiation and/or heating, and a step of removing the die from the cured curable composition for transfer materials. Each of the steps is described below.

<1. Applying Step>

A process for applying the curable composition to the substrate is not particularly limited and, for example, a process such as spin coating or dip coating can be used. A process capable of forming a film of the curable composition for transfer materials which has a uniform thickness on the substrate is preferably used. FIG. 1(a) shows a state in which the substrate is coated with the curable composition according to the present invention.

<2. Transferring and Curing Steps>

The micropattern can be formed by pressing (transferring) the die, in which a fine pattern has been already formed, to a coated film of the curable composition according to the present invention. After the die is pressed to the coated film, the curable composition is cured with the energy ray or is thermally cured. Alternatively, the both methods may be used in combination, that is, the curable composition may be irradiated with the energy ray while being heated. FIGS. 1(b) and 1(c) show the step of pressing the die to the curable composition of the present invention applied to the substrate and the step of curing the composition by energy ray irradiation and/or heating, respectively.

A material for the die is not particularly limited. In the case of curing the curable composition with an energy ray such as an ultraviolet ray, the die is preferably made of resin, glass, or quartz which transmits the energy ray, because even if the substrate transmits no energy ray, the micropattern can be formed in such a manner that the energy ray is applied to the curable composition in a direction from the die to the substrate and thereby the curable composition is cured.

An atmosphere used during pressing the die, or thereafter applying heat or irradiating the energy ray, is not particularly limited and is preferably a vacuum in order to prevent bubbles from remaining in the cured curable composition. When the functional group of the curable composition is a carbon-carbon double bond such as a (meth)acrylic group, an allyl group or a vinyl group, it is preferred that, in a vacuum, the die be pressed and thereafter heat be applied or the energy ray be irradiated to prevent inhibition of polymerization by oxygen.

<3. Die-Removing Step>

After the coated film which consists of the curable composition according to the present invention is cured, the die is removed from the coated film. The micropattern may be heated in order to enhance the heat resistance and physical strength of the micropattern after the removal of the die. A method for the heating is not particularly limited. The formed pattern is gradually heated to a temperature not higher than the glass transition temperature of the coated film so as not to be broken. The upper limit of the heating temperature thereof is preferably set at 250° C. for the purpose of preventing thermal decomposition of the coated film.

The micropattern with a size of 10 μm or less is formed as described above. The micropattern results from the curing of the curable composition for transfer materials according to the present invention and has high selectivity on etching rates regarding a fluorine-based gas and an oxygen gas. Therefore, a micropattern formed by the method for forming a micropattern with a size of 10 μm or less has high resistance to a gas used in etching; hence, the degree of etching can be readily controlled. The micropattern has low resistance to gas used to remove the micropattern and therefore can be readily removed with the gas used for the removal. Accordingly, the micropattern acts as a good resist and therefore can be used for various applications including semiconductors and magnetic recording media.

EXAMPLES

The present invention is further described below in detail with reference to examples. The present invention is not limited to the examples.

Example 1

Into a three-necked flask equipped with a thermometer and a cooling tube, 2.0 g (8.3 mmol) of 1,3,5,7-tetramethylcyclotetrasiloxane, 6.4 g (34.9 mmol, 1.05 times on the basis of Si—H groups) of allyl 3,4-epoxycyclohexanecarboxylate and 50 g of toluene were added, followed by stirring at room temperature under an Ar stream. To the mixture, 0.82 g (the weight amount of metallic platinum was 1,000 ppm with respect to the charged raw materials) of a 2% xylene solution of a platinum-divinyltetramethyldisiloxane complex was slowly added in four batches. After the mixture was stirred at room temperature for two hours, toluene was vacuum-distilled off therefrom. An obtained residue containing reactants was dissolved in propylene glycol monomethyl acetate such that a solution with a solid concentration of 5% was obtained.

A cationic photopolymerization initiator, triphenylsulfonium hexafluoroantimonate, was added to and was dissolved in the obtained solution such that the added amount was 2 parts by mass with respect to 100 parts by mass of a solid component in the solution, followed by filtration with a 0.2 μm filter, whereby a curable composition for transfer materials was obtained. On a glass substrate set in a spin coater, 0.5 ml of the obtained curable composition was dropped. The glass substrate was rotated at 500 rpm for 5 seconds, at 3,000 rpm for 2 seconds, and then at 5,000 rpm for 20 seconds, whereby a thin film was formed on the glass substrate. The thin film was placed under a nitrogen stream and was irradiated with an ultraviolet ray, whereby the thin film was cured. The resulting cured film was measured for reactive ion etching rates of a $CF_4$ gas and an oxygen gas.

(Procedure for Measuring Etching Rate)

A piece of glass was attached to the cured film and an etching treatment was carried out by a reactive ion etching apparatus under the following conditions. The glass piece was removed and the difference in level between an etched portion of the thin film and a portion of the thin film that was protected by the glass piece was measured.

Etching rate(nm/s)=difference in level(nm)÷treatment time(s)

Reactive Ion Etching Conditions
(Fluorine-Based Gas)
 Etching gas: carbon tetrafluoride
 Pressure: 0.5 Pa
 Gas flow rate: 40 sccm
 Plasma voltage: 200 W
 Bias voltage: 20 W
 Treatment time: 20 s (Oxygen Gas)
 Etching gas: oxygen
 Pressure: 0.5 Pa
 Gas flow rate: 40 sccm
 Plasma voltage: 200 W
 Bias voltage: 20 W
 Treatment time: 600 s Comparative Example 1

The following compounds were dissolved in 1,000 parts by mass of propylene glycol monomethyl ether acetate which was used as a solvent: 100 parts by mass of triethylene glycol diacrylate and 3 parts by mass of a polymerization initiator, 2-hydroxy-2-cyclohexylacetophenone. The obtained solution was filtered through a 0.2 μm filter. On a glass substrate set in a spin coater, 0.5 ml of the filtered solution was dropped. The glass substrate was rotated at 500 rpm for 5 seconds, at 3,000 rpm for 2 seconds, and then at 5,000 rpm for 20 seconds, whereby a thin film was formed on the glass substrate. The thin film was placed under a nitrogen stream and was irradiated with an ultraviolet ray, whereby the thin film was cured. The cured film was measured for reactive ion etching rates of a $CF_4$ gas and an oxygen gas in the same manner as that described in Example 1.

The reactive ion etching rates determined using respective gases in Example 1 and Comparative Example 1 and the ratios thereof are summarized in Table 1.

TABLE 1

|  | Example 1 | Comparative Example 1 |
|---|---|---|
| $CF_4$ gas etching rate (nm/s) | 1.20 | 1.22 |
| Oxygen etching rate (nm/s) | 0.10 | 3.48 |
| $CF_4/O_2$ ratio | 12.0 | 0.35 |

($CF_4/O_2$ ratio) = ($CF_4$ gas etching rate) ÷ (Oxygen etching rate)

Table 1 shows that the cured film obtained by curing the curable composition in Example 1 had a $CF_4$ gas etching rate higher than an oxygen etching rate and therefore had extremely high selectivity on etching rates.

Example 2

Figure 2:
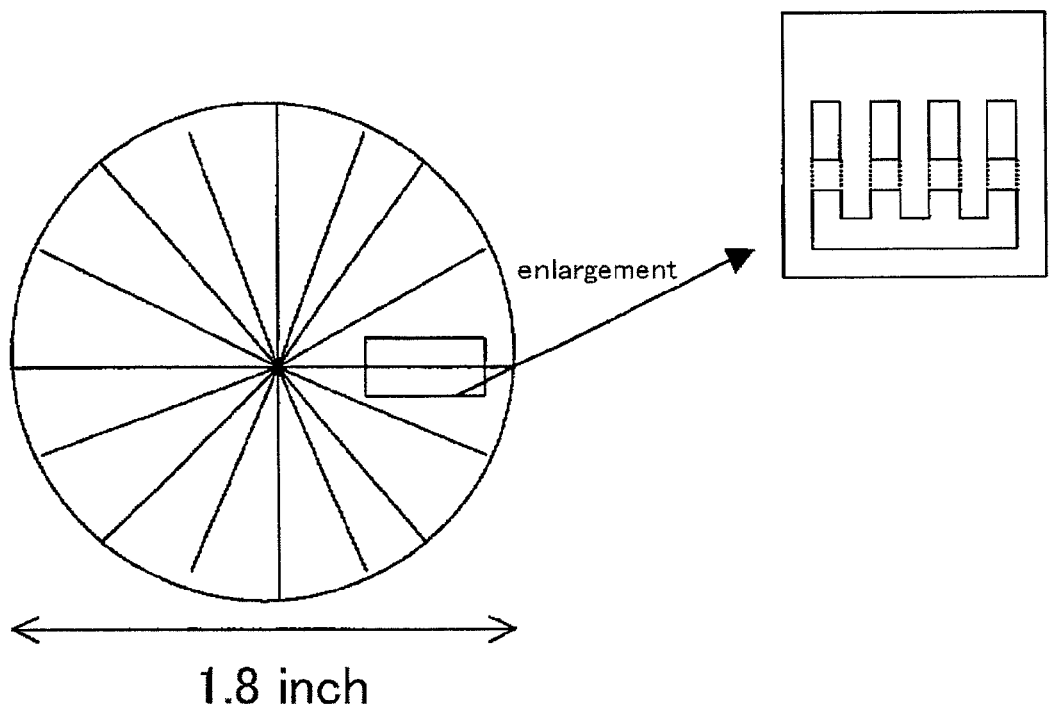
FIG. 2 is an illustration of a disk, which is made of quartz glass which has been patterned with a concave and convex shape along the radial direction in Example 2. The disk has a diameter of 1.8 inches. The concave portions have a width (L) of 80 nm in the radial direction in FIG. 1 and a depth of 150 nm. The convex portions have a width (S) of 120 nm in the radial direction in the figure. A rectangle corresponding to a die shown on the upper right side of a circular glass substrate shown in FIG. 2 has a vertical (shorter hand) length of 0.1 mm.

On a glass substrate set in a spin coater, 0.5 ml of the curable composition for transfer materials obtained in Example 1 was dropped. The glass substrate was rotated at 500 rpm for 5 seconds, at 3,000 rpm for 2 seconds, and then at 5,000 rpm for 20 seconds, whereby a thin film was formed on the glass substrate. The following disk was provided on a surface of the thin film formed on the glass substrate: a disk which was made of quartz glass which had been patterned with a concave and convex shape along radial direction thereof as shown in FIG. 2. The glass substrate was set in a UV nanoimprint press apparatus, ST50, (manufactured by Toshiba Machine Co., Ltd.) and was then pressed. The thin film was irradiated with ultraviolet light having a wavelength of 365 nm and an intensity of 6.5 mW through the quartz glass-made disk. The concave portions of the disk had a depth of 150 nm. After the quartz glass-made disk was taken out of the press apparatus, the thin film on the glass disk was observed. This showed that there were no defects such as pattern defects and ununiform portion on the coated film.

Figure 3:
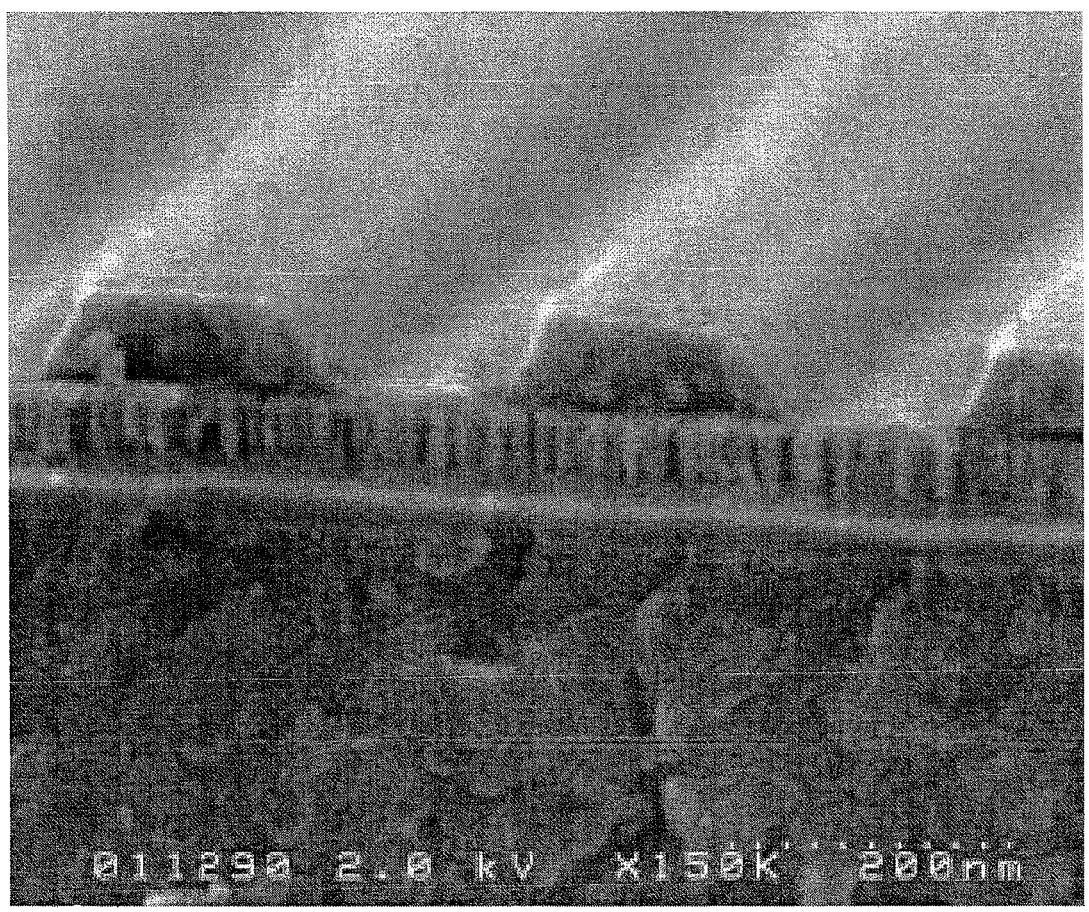
FIG. 3 is a field emission electron micrograph of a cross section of a glass substrate which was broken after a pattern shape had been transferred to a thin film in Example 2.

FIG. 3 shows results obtained by observing a cross section of the glass substrate which was cut after the pattern shape was transferred to the thin film, using a field emission electron microscope. As shown in FIG. 3, the use of the curable composition of Example 2 allows a rectangular shape to be very well transferred.

Comparative Example 2

Methyltrimethoxysilane (24.5 g, 0.18 mol), tetramethoxysilane (27.4 g, 0.18 mol), 2-(3,4-epoxycyclohexyl)ethyltrimethoxysilane (44.3 g, 0.18 mol) and 70 g of propylene glycol monomethyl ether acetate were charged into a three-necked flask equipped with a thermometer and a cooling tube. To the flask, 29.8 g of dilute nitric acid with a concentration adjusted at 0.25% by weight was slowly added over one hour while stirring with a stirrer at room temperature.

After the mixture was stirred at room temperature for 24 hours, methanol and water produced by the reaction were distilled off from the mixture at a pressure of 7 kPa by heating in a 50° C. water bath. To the resulting mixture, 200 g of propylene glycol monomethyl ether acetate was added, followed by well mixing. Then, the mixture was filtered through a 0.2 μm filter, whereby a mixed liquid was obtained. On a glass substrate set in a spin coater, 0.5 ml of the mixed liquid was dropped.

Figure 4:
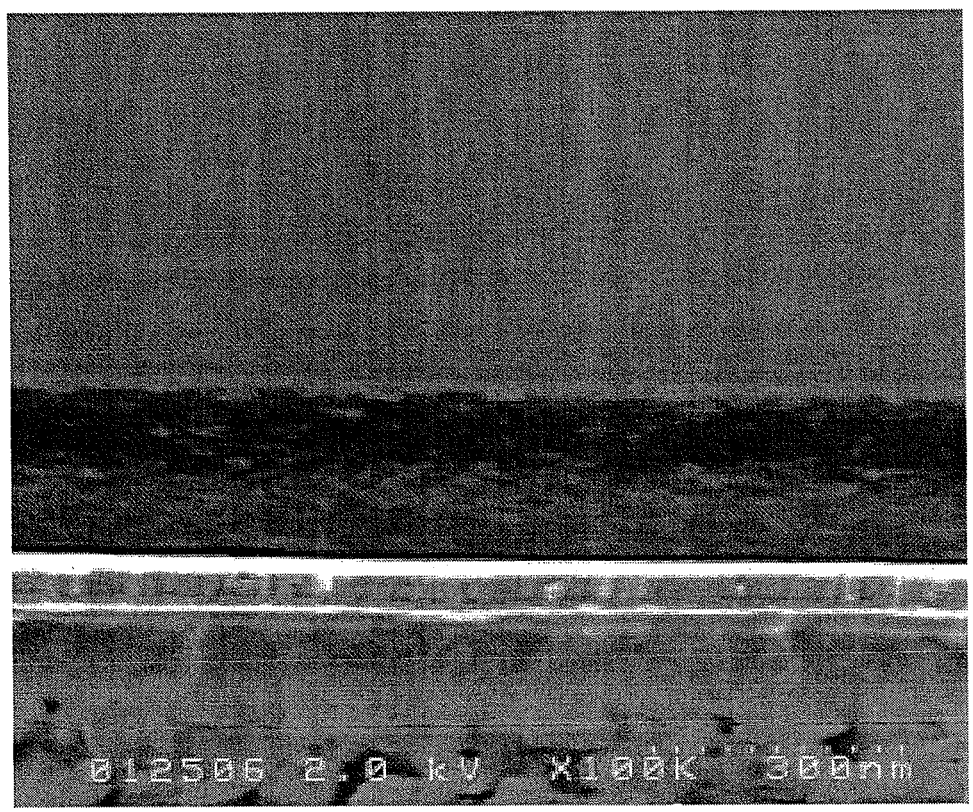
FIG. 4 is a field emission electron micrograph of a cross section of a glass substrate which was irradiated with ultraviolet light and was then broken in Comparative Example 2.

The glass substrate was rotated at 500 rpm for 5 seconds, at 3,000 rpm for 2 seconds, and then at 5,000 rpm for 20 seconds, whereby a thin film was formed on the glass substrate. Next, a die, made of quartz glass, having a patterned surface shown in FIG. 2 was provided on a surface of the prepared glass substrate on which the mixed liquid was coated in the same manner as that described in Example 2, the patterned surface being directed downward. The glass substrate was set in a UV nanoimprint press apparatus, ST50, (manufactured by Toshiba Machine Co., Ltd.) and was then pressed. The thin film was irradiated with ultraviolet light having a wavelength of 365 nm and an intensity of 6.5 mW. FIG. 4 shows results obtained by observing a cross section of the glass substrate which was irradiated with ultraviolet light and which was then broken, using a field emission electron microscope. Any rectangular shape was not observed at all, which showed that a transfer fault occurred.

The thin film was left at room temperature for 14 days, so that precipitate was formed in a part of the film. The precipitate was a gel produced by the polymerization of hydrolysate produced from the alkoxysilane. Therefore, it is difficult to use a curable composition obtained in Comparative Example 2 as a stable composition for imprints.

Example 3

Under a nitrogen atmosphere, the following materials were charged into a three-necked 1L flask, equipped with a thermometer, a dropping funnel, a stirrer and a Dimroth condenser, placed in a oil bath: 155.78 (g) of (meth)allyl 3,4-epoxycyclohexane-1-carboxylate, 108.32 (g) of toluene and 0.0260 (g) of a Pt-VTS catalyst (an isopropyl alcohol solution containing a divinyltetramethyldisiloxane-platinum complex and having a platinum concentration of 3%).

Stirring was started and the internal temperature of the flask was adjusted at 60 (° C.). To the flask, 51.42 (g) of 1,3,5,7-tetramethylcyclotetrasiloxane was added dropwise over 5 hours in such a manner that the internal temperature was controlled so as not to exceed 61° C. After dropwise addition was finished, the mixture was aged at 60° C. for one day and was then subjected to GC analysis, thereby confirming that there was no peak corresponding to 1,3,5,7-tetramethylcyclotetrasiloxane which was a raw material.

After aging was finished, toluene which was used as a solvent, was distilled off with a rotary evaporator, whereby 207.19 (g) of a crude product was obtained. The crude product was purified with a molecular distillation unit (MS-FL Tokugata, manufactured by Taika Kogyo Co., Ltd.), whereby 150.10 (g) of a product was obtained.

Figure 5:
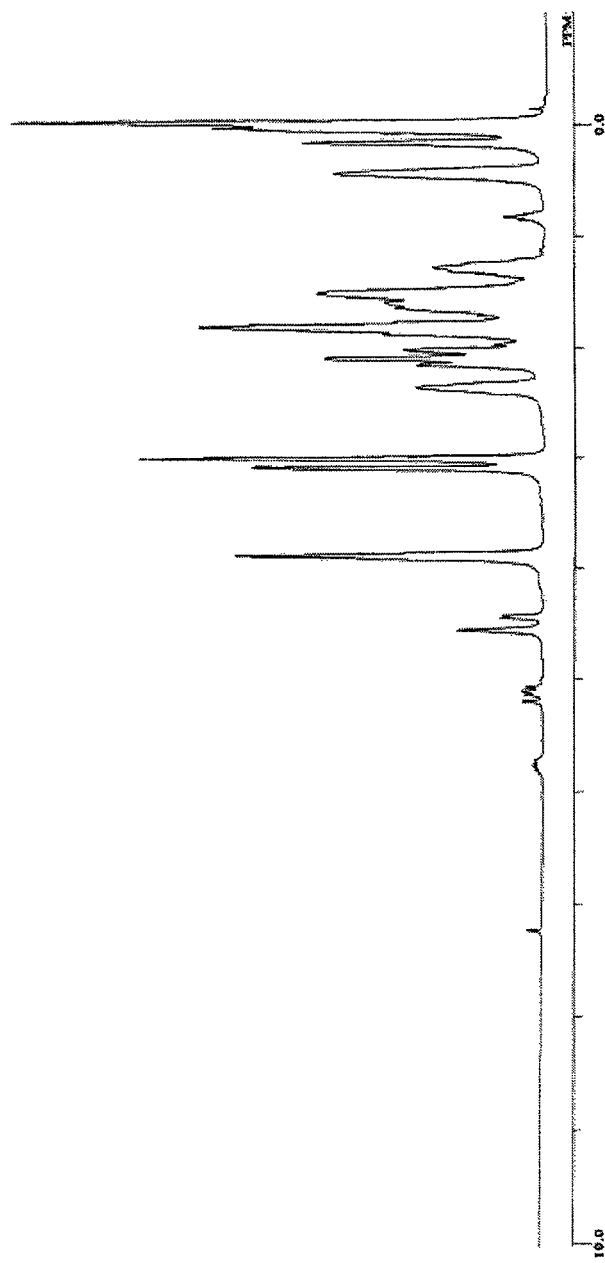
FIG. 5 is a $^1$H-NMR chart of a product obtained in Example 3.
Figure 6:
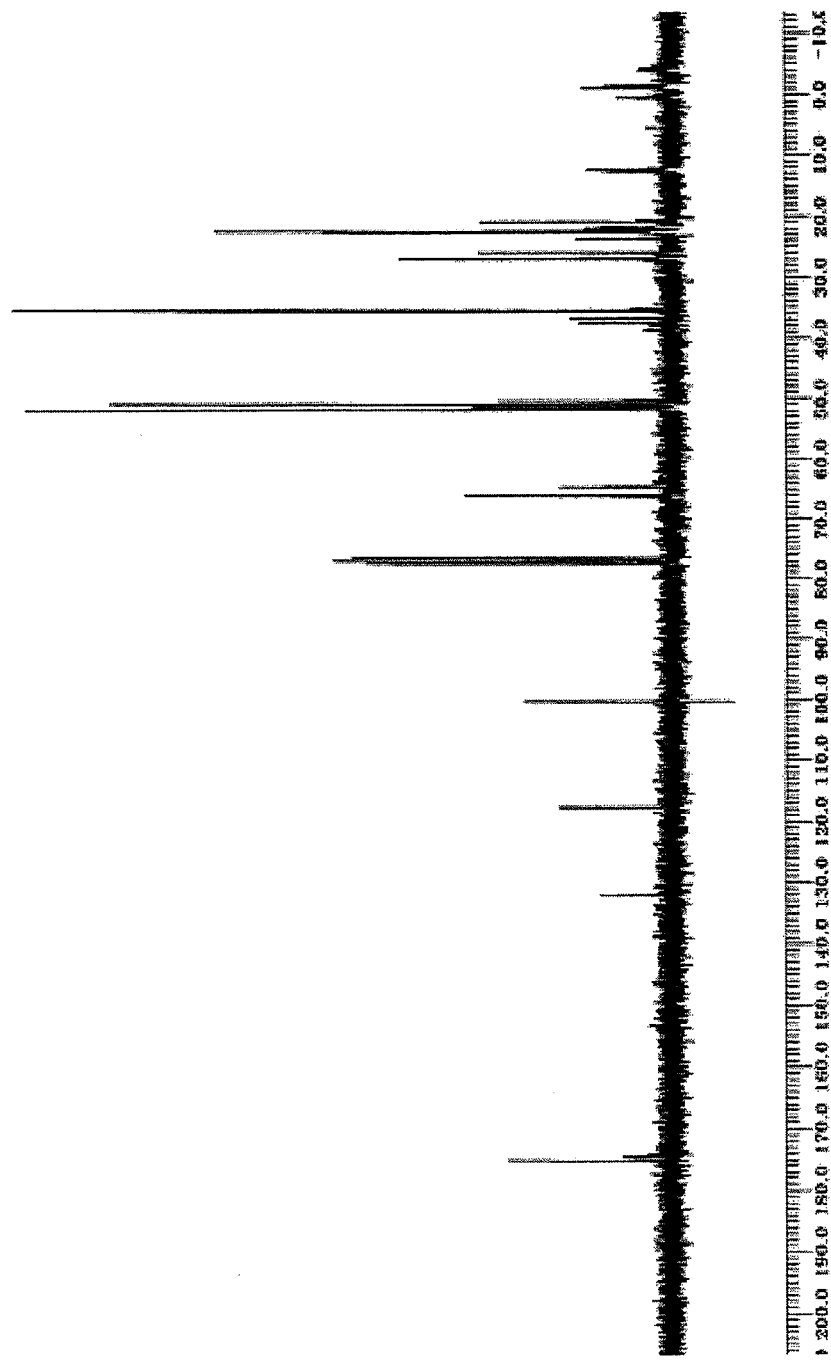
FIG. 6 is a $^{13}$C-NMR chart of the product obtained in Example 3.
Figure 7:
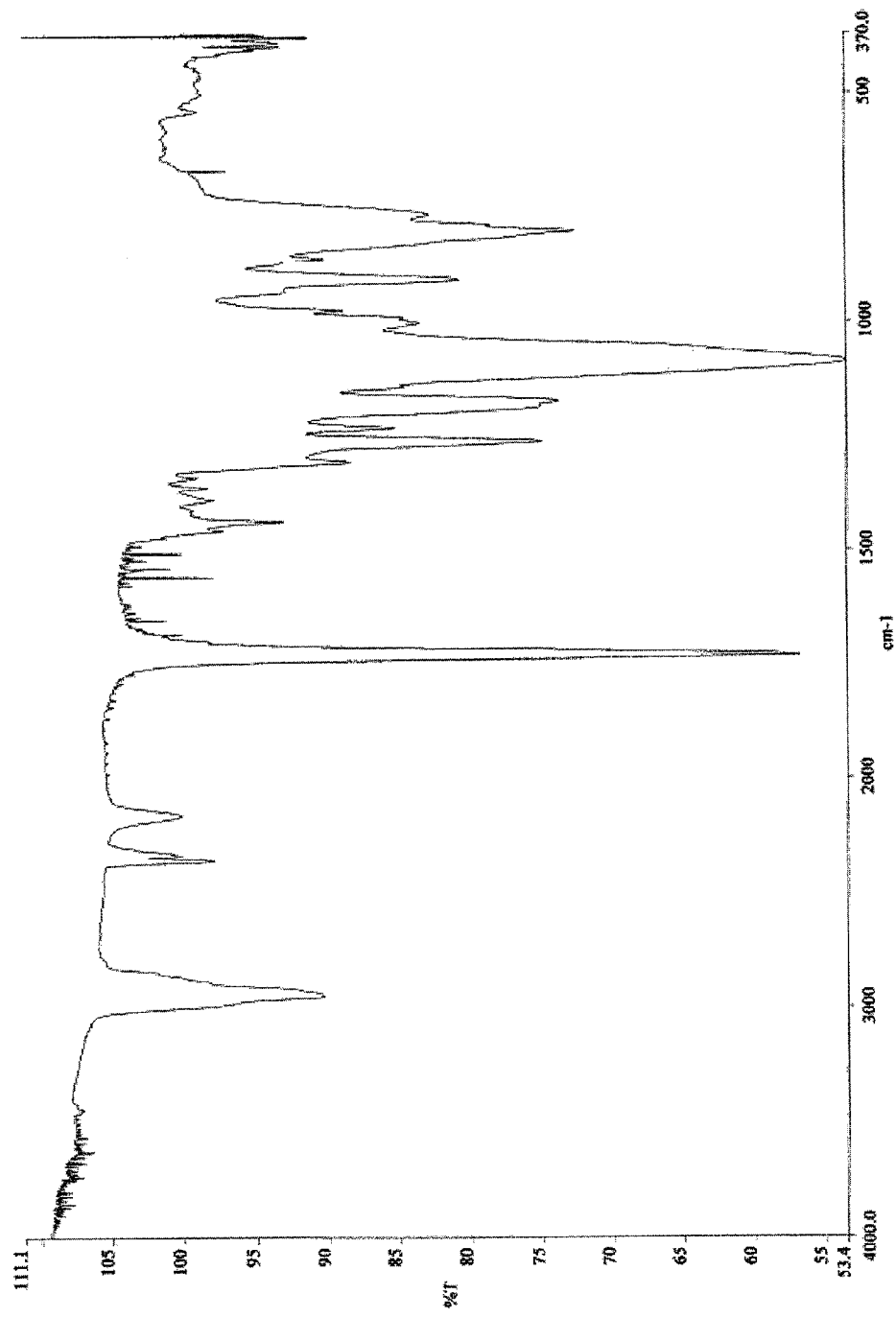
FIG. 7 is an IR chart of the product obtained in Example 3.

The product was analyzed by $^1$H-NMR, $^{13}$C-NMR and IR. The analysis results are shown in FIGS. 5 to 7 (FIG. 5 is a $^1$H-NMR chart, FIG. 6 is a $^{13}$C-NMR chart, and FIG. 7 is an IR chart).

The obtained spectra were analyzed. The results obtained by $^1$H-NMR analysis showed a peak at 2 (ppm) assigned to an alicyclic epoxy. Likewise, the results obtained by $^{13}$C-NMR analysis showed a sharp peak at around 50 (ppm) originating from an epoxy in epoxycyclohexane. The results obtained by IR analysis showed an absorption peak at 1,172 cm$^{-1}$ originating from the alicyclic epoxy; an absorption peak at 1,732 cm$^{-1}$ originating from an ester carbonyl; and a characteristic absorption peak at 1,057 cm$^{-1}$ originating from Si—O.

From the above analysis results, the obtained product could be confirmed to be a desired compound represented by the following structure.

[Chem. 14]

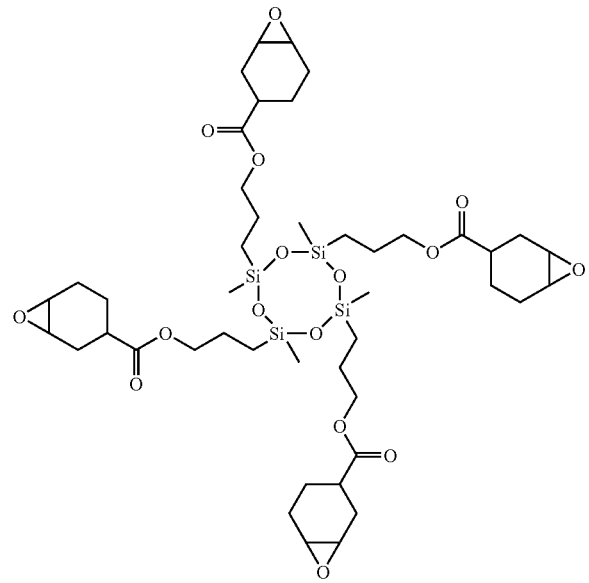

The invention claimed is:

1. A curable composition for transfer materials containing a curable silicon compound wherein the curable silicon compound is an epoxy group-containing organosiloxane compound represented by the following general formula (1), (2), or (3):

[Chem. 1]

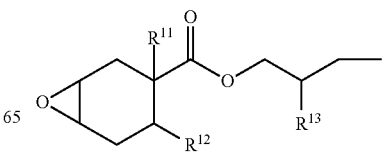

(1)

-continued

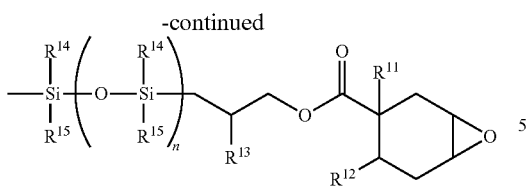
(2)
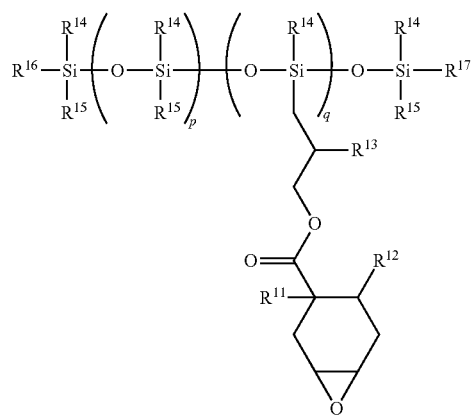

[Chem. 3]
(3)
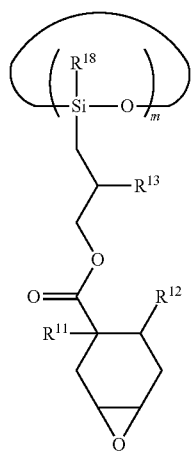

wherein $R^{11}$ is a hydrogen atom or a methyl group; $R^{12}$ is a hydrogen atom, a methyl group or a phenyl group; $R^{13}$ is a hydrogen atom or a methyl group; $R^{14}$ and $R^{15}$ are independently a substituted or unsubstituted monovalent hydrocarbon group having 1 to 10 carbon atoms; $R^{16}$ and $R^{17}$ are independently a substituted or unsubstituted monovalent hydrocarbon group having 1 to 10 carbon atoms or a monovalent hydrocarbon group represented by the following general formula (4); $R^{18}$ is a hydrogen atom, a methyl group, an ethyl group or a phenyl group; n and q are each an integer of one or more; p is an integer of 0 or more; and m is an integer of 3 to 6:

[Chem. 4]
(4)
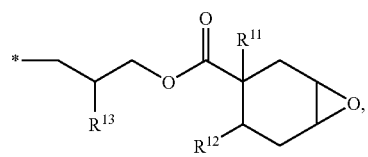

where $R^{11}$ is a hydrogen atom or a methyl group; $R^{12}$ is a hydrogen atom, a methyl group, or a phenyl group; $R^{13}$ is a hydrogen atom or a methyl group; and * represents a bond.

2. A curable composition for transfer materials containing a curable silicon compound produced by subjecting a silicon compound (A) having a Si—H group and a compound (B) having a curable functional group and a carbon-carbon double bond other than the curable functional group to a hydrosilylation reaction, and a photopolymerization photoinitiator, wherein the compound (B) is at least one compound represented by the following formulas (a) to (d):

[Chem. 5]

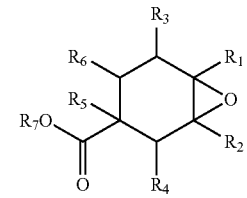
(a)

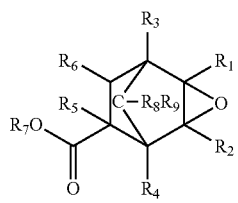
(b)

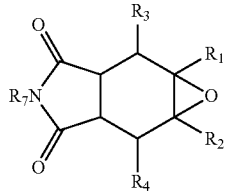
(c)

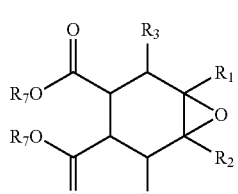
(d)

wherein $R_1$ to $R_5$, $R_8$ and $R_9$ are each independently hydrogen or a methyl group; $R_6$ is hydrogen, a methyl group or a phenyl group; and $R_7$ is an allyl group, a 2-methyl-2-propenyl group, a 3-butenyl group or a 4-pentenyl group, wherein the compound (A) is a cyclic siloxane compound.

* * * * *